United States Patent [19]
Kalb et al.

[11] Patent Number: 5,287,960
[45] Date of Patent: Feb. 22, 1994

[54] BLOOD PRODUCT DISPOSAL SYSTEM AND METHOD

[76] Inventors: Irvin M. Kalb, 327 Alta Ave., Santa Monica, Calif. 90402; Robert H. Shaw, 243 Peck Dr., Beverly Hills, Calif. 90212; Michael J. Ram, 1 Horseshoe Rd., Bell Canyon, Calif. 91307

[21] Appl. No.: 963,996

[22] Filed: Oct. 20, 1992

[51] Int. Cl.$^5$ ............................................. B65D 81/18
[52] U.S. Cl. .................................. 206/210; 206/440; 383/66; 383/86; 604/385.1
[58] Field of Search .................. 206/438–440, 206/204, 205, 210, 494; 383/66, 86; 604/358, 385.1

[56] References Cited

U.S. PATENT DOCUMENTS

| | | | |
|---|---|---|---|
| 3,181,583 | 5/1965 | Lingenfelter | 383/66 X |
| 3,331,499 | 7/1967 | Jost | 206/210 |
| 3,702,677 | 11/1972 | Heffington | 206/205 X |
| 4,182,336 | 1/1980 | Black | 206/438 X |
| 4,417,658 | 11/1983 | Gardner et al. | 206/438 |
| 4,576,278 | 3/1986 | Laiewski et al. | 206/204 |
| 4,709,399 | 11/1987 | Sanders | 383/66 |
| 4,735,316 | 4/1988 | Fröidh et al. | 206/438 |
| 4,765,477 | 8/1988 | Fröidh et al. | 206/438 |
| 4,815,590 | 3/1989 | Peppiatt et al. | 206/204 |
| 4,865,855 | 9/1989 | Hansen | 206/204 X |
| 4,927,010 | 5/1990 | Kannankent | 206/204 |
| 5,193,684 | 3/1993 | McDonald | 206/438 A |

FOREIGN PATENT DOCUMENTS 2452769 5/1976 Fed. Rep. of Germany ...... 206/210

*Primary Examiner*—Bryon P. Gehman
*Attorney, Agent, or Firm*—Michael J. Ram

[57] ABSTRACT

The present invention relates to a method for treating and disposing of materials contaminated with blood such as blood soaked menstrual pads or tampons. The invention further relates to a system for decontaminating and disposing of blood soaked products comprising a bag containing a disinfecting material, the bag having a readily openable portion for placing the blood soaked product into the bag and in contact with the disinfecting material and then resealing the bag to prevent its contents from contaminating the surroundings. Once resealed, the seal can not be removed without destroying the seal.

8 Claims, 2 Drawing Sheets

BLOOD PRODUCT DISPOSAL SYSTEM AND METHOD

BACKGROUND

The present invention relates to a method for treating and disposing of materials contaminated with blood or blood products and devices and materials for use in the process.

Many diseases are transmitted between humans by contact of open wounds or sores with contaminated blood. Other diseases can be transmitted by insects, such as flies, fleas or mosquitoes, which feed on contaminated blood or materials which contain blood. These insects then contact the open wounds or sores on humans, bite or sting individuals or animals, or, as for example in the case of fleas on rodents, travel into living quarters of humans where the fleas can then transfer to humans, thus transmitting viruses, germs, bacteria, parasites or other disease vectors to the individual. Diseases known to be transmitted by contact with blood or which can be carried by insects are hepatitis, HIV, AIDS, malaria, herpes, human papilloma virus (HPV), and Jacobs Kreutzfelds disease. Many other diseases of unknown etiology are believed to be transmitted by insect bites or contact with infected blood.

Over the last several years considerable efforts have been taken to eliminate or significantly reduce the possibility of transmission of blood bourn diseases by casual contact in the hospital or medical facility environment. Additionally, strict testing and controls have been placed on blood and blood products which are transfused during medical procedures. However, no attempts have been made to eliminate the possibility of the transmission of blood bourn diseases or the contamination of ground water supplies which can be caused by the casual or negligent disposal of menstrual blood. On a monthly basis, millions of women dispose of blood soaked tampons or pads in garbage receptacles or flush them down toilets. These blood soaked materials then end up in land fills or sewer systems where insects and other vermin can contact these blood soaked products. Unfortunately, if the woman's menstrual blood contains germs, bacteria, viruses, or blood parasites, these microorganisms can survive the disposal conditions and can then be transmitted to other humans. This is of particular concern in the case of HIV, hepatitis A, B, or C and HPV which are known to be transmitted in blood and which are believed to survive normal disposal conditions. Additionally, many diseases endemic to the less developed third world but virtually unknown in the developed countries of the world can be readily introduced into those developed countries by a single menstruating woman entering the country from those regions. This is a problem currently unrecognized or unaddressed by the world's public health authorities.

Thus, there is a need for a simple, safe and effective method and system to readily destroy microorganisms carried in menstrual blood and to allow safe disposal of menstrual blood.

SUMMARY

The present invention is directed to methods and devices that respond to these needs and address the deficiencies of the present methods for disposal of menstrual blood.

These needs are met by the present invention which comprises a method of contacting and permeating a blood soaked pad or tampon with a microorganism destroying compound, such as peroxide releasing compounds, chlorine solutions, chlorine releasing compounds, iodine solutions, and other disinfecting materials, the blood soaked pad or tampon and microorganism destroying compound being sealed within a non-porous container until the infective nature of the microorganism has been eliminated and/or the container and its contents can be safely destroyed. In a preferred embodiment, the method comprises placing a chlorine containing chemical, which can be carried by a porous substrate, into direct contact with the blood containing absorbent pad and sealing the chlorine/pad combination in a leak proof plastic bag.

These needs are further met by products and devices for delivering microorganism destroying materials and containers designed for performing the decontamination process. In a preferred embodiment, the chlorine is delivered from a sodium hypochlorite soaked sponge or a substrate impregnated with or carrying a dry chlorine releasing compound such as trichloro s-triazinetrione.

DRAWINGS

These and other features, aspects and advantages of the present invention will become better understood with reference to the following description, appended claims, and accompanying drawings, where:

DESCRIPTION

The most common methods for collecting menstrual blood are the insertion of an absorbent tubular tampon into the vagina of the menstruating female or the placement of an absorbent pad external over the opening of the vagina during the period of menstrual flow. The tampon or pad, which is replaced frequently during the period of menstrual flow, usually contains from about 1 cc to about 5 cc of blood or other vaginal secretions, with the normal menstrual flow totaling from about 3 cc to about 10 cc per day with an average flow during each period of menstruation of from about 25 cc to about 55 cc.

Literature has indicated that a 0.1% solution of chlorine, when brought in direct contact with the HIV virus, is adequate to kill the virus. However, to assure complete penetration of the disinfectant into the pad carrying the menstrual blood, a higher concentration of chlorine is beneficial. It has been found that the use of about 5 to about 7.5 cc of a 5% sodium hypochlorite solution or about 0.75 g to about 1.25 g of a dry powdered trichloro s-triazinetrione, which contains 45.77% chlorine, 90% of that amount being available as free chlorine, when brought into contact with liquid blood soaked into a pad or tampon, and contact is maintained for a minimum of about fifteen minutes, results in most infectious matter in the blood being destroyed or at least incapable of infecting other organisms, thus eliminating or significantly reducing the risk of contamination from the microorganisms in the blood. However, to assure complete decontamination, it is preferred that excess chlorine be used and the blood soaked absorbent material be sealed with the excess chlorine in a closed container, such as a plastic bag, for a period in excess of fifteen minutes. Additionally, the use of peroxide releasing materials is effective against anaerobic bacteria.

FIGS. 1-6 show an embodiment of the system which includes features of the invention, namely a sponge at least partly saturated with a chlorine containing compound, such as sodium hypochlorite, sealed in a plastic bag to prevent evaporation of the water in the solution, oxidation of the chlorine compound or loss of the chlorine. The bag includes means for ready access to the liquid containing sponge when it is time to dispose of a blood containing pad or tampon, and is sized to receive both the blood soaked pad and the sponge. Additionally, the bag is designed to be readily sealed after a pad is placed into it. Preferably, once the bag is resealed, the seal can not be reopened without tearing or cutting the bag, thus preventing access to the contaminated contents.

Figure 1:
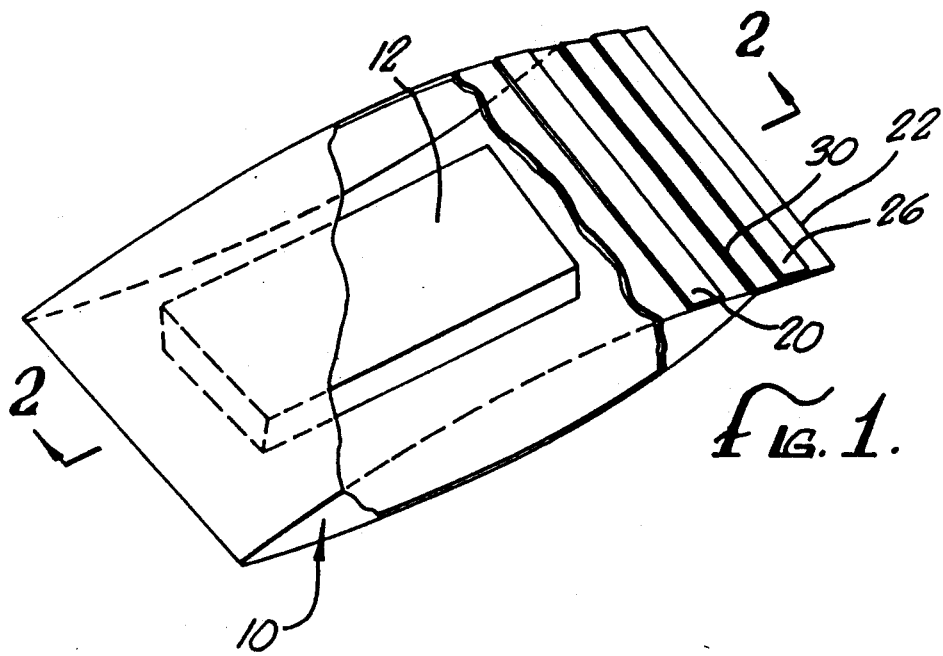
FIG. 1 is a partly cutaway perspective top view of the disposal system embodying features of the invention.
Figure 2:
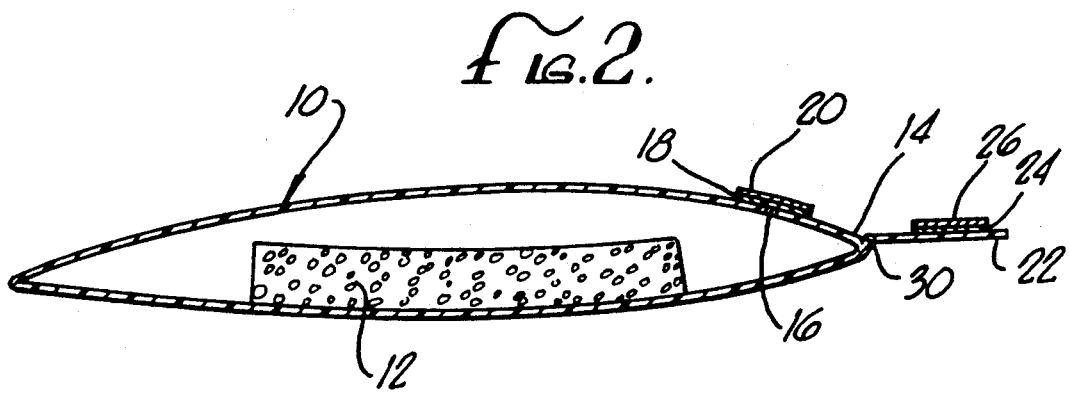
FIG. 2 is a cross sectional view of the disposal system of FIG. 1 taken along line 2—2 of FIG. 1.
Figure 3:
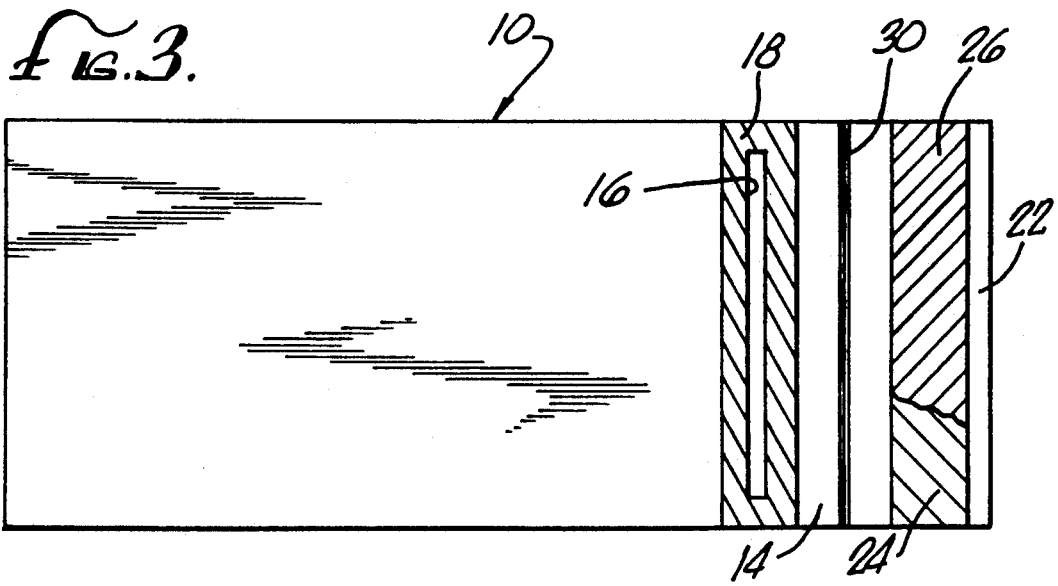
FIG. 3 is a top view of the disposal system of FIG. 1 after the bag is opened.

FIG. 1 shows the liquid and gas impervious bag 10 having a disinfectant containing structure 12 enclosed therein. In a particular embodiment the disinfectant containing structure 12 is a sponge containing a chlorine containing liquid. Spaced a short distance from a first end 14 of the bag 10 is a slit 16. The slit is surrounded on all sides by a first contact adhesive 18 and the adhesive 18 is covered by a readily removable sealing strip 20. As can best be seen in FIG. 3, in a particularly preferred embodiment, the slit 16 does not traverse the entire width of the bag so that the adhesive 18 and sealing strip 20 totally surrounds the slit opening. Above the upper end 14 of the bag 10 is a sealing flap 22 which has, on its upper surface, a second strip of contact adhesive 24 compatible with the first contact adhesive 18, the second contact adhesive being covered by a protective release paper 26. While the use of the second strip of contact adhesive 24 is not necessary for the operation of the system, the use of the two adhesive strips 18 and 24 makes for a more positive sealing of the bag during reclosure as discussed below.

Figure 4:
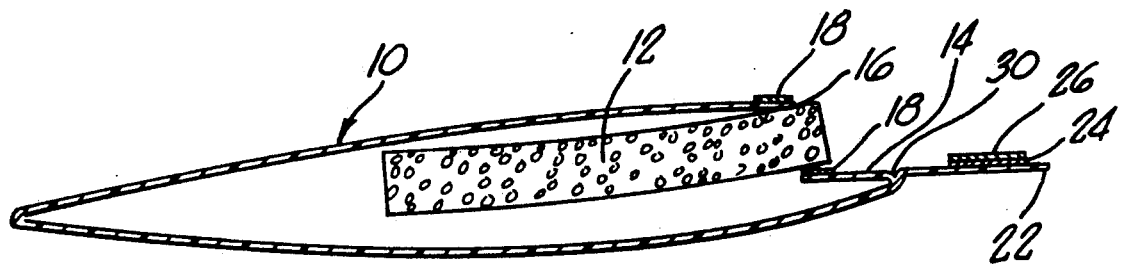
FIG. 4 is a cross sectional view of the disposal system of FIG. 1 taken along line 2—2 of FIG. 1 showing the contents of the plastic bag partly removed.
Figure 5:
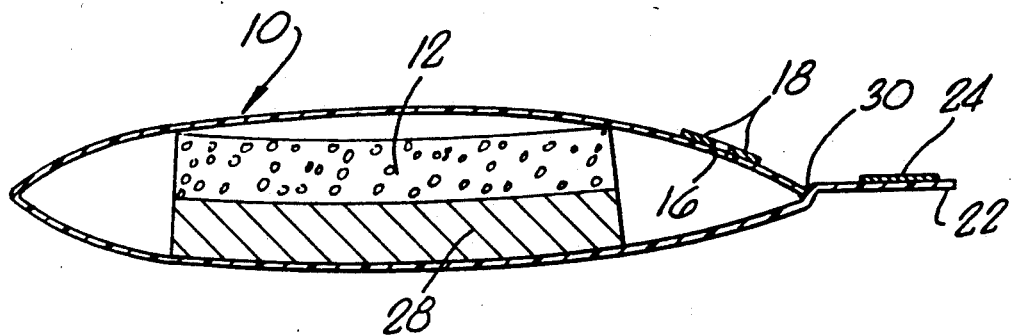
FIG. 5 is a cross sectional view of the disposal system of FIG. 1 taken along line 2—2 of FIG. 1 showing the bag after a blood contaminated pad is inserted therein.
Figure 6:
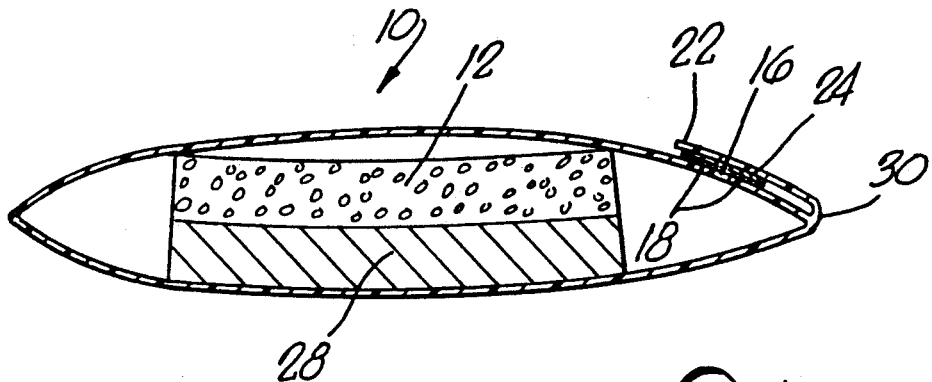
FIG. 6 is a cross sectional view of the disposal system of FIG. 1 taken along line 2—2 of FIG. 1 showing the bag after a blood contaminated pad is inserted therein and the bag is sealed for disposal.

To use the system the sealing strip 20 is removed from the surface of the bag 10 (FIG. 3) and the liquid containing sponge 12 is removed from the bag 10 (FIG. 4). The blood containing tampon or pad 28 is then removed from its collection site, the blood containing surface is brought into contact with the sponge 12 and the sponge 12 and pad 28 are inserted through the slit 16 into the bag 10 (FIG. 5). The release paper 26 is then removed, the sealing flap 22 is folded along the heat seal 30 and the first and second contact adhesives 18, 24 are brought into contact causing an immediate bond between the two adhesives, thus sealing the slit 16 in a leak proof manner (FIG. 6). As soon as the disinfecting material, such as a chlorine containing compound in the sponge 12, comes into contact with the blood in the pad 28, a reaction starts to take place between microorganisms in the blood and the chlorine or other disinfecting material, eventually killing the microorganism.

While a non-porous bag, formed from a plastic material such as a polyethylene, polypropylene or similar materials is preferred, other non-porous materials or combinations of materials may be used. For example, the bag can be formed from a multilayered film material which utilizes a non-porous barrier material such as nylon, saran, or wax. In such an instance, the non-porous barrier material can be coated onto a porous packaging material such as paper, cardboard, or porous polymeric materials such as Tyvek non-woven material. Such a combination of materials has the benefit of being more biodegradable when disposed of in a land fill or less polluting when incinerated.

Additionally, while a first adhesive 18 and sealing strip 20 placed on the wall of the bag 10 are disclosed, other opening means can be used. For example, the bag may include a tear strip imbedded in the wall of the bag 10. Pulling the tear strip creates the opening in the wall of the bag.

The disinfectant containing structure 12 can formed from various different materials. In a first embodiment the disinfecting agent is a liquid and the carrier is a porous material, preferably spongy in nature so that in use it can be compressed to aid in driving the disinfectant from the carrier into the pad containing the menstrual blood once sealed in the bag. In an alternative embodiment, the disinfectant is a dry material entrapped in a porous structure, coated on a carrier material or formed into a sheet. The sheet of the dry disinfectant material can be formed by casting the material from solution, compressing powdered material or casting the material in combination with a noninterferring binder such as a wax or a water soluble polymer. Where the disinfectant is delivered in a dry form, while contact with dry blood can be effective, the more effective procedure is to use the liquid blood in the menstrual pad to dissolve and/or activate the dry disinfectant.

In a third embodiment the disinfectant containing structure 12 comprises the disinfectant, whether in a liquid or a dry form, enclosed in a frangible package or capsule. In use, the frangible package or capsule is broken while next to or in contact with the blood soaked menstrual pad, thus releasing the contents of the package or capsule onto the menstrual pad. The capsule or package can be loosely contained in the disposable bag, supplied separately, or attached to or incorporated in the bag wall in a manner that will make its contents available when required.

Although the present invention has been described in considerable detail with reference to certain preferred versions and uses thereof, other versions and uses are possible. For example, the primary application is for the disposal of blood containing menstrual pads. However, the invention is applicable to the disposal of other blood containing materials such as bandages, surgical sponges, and the like, or the disposal of materials soaked with other potentially contaminated body fluids such as urine, sputum, or mucous. Therefore, the spirit and scope of the appended claims should not be limited to the description of the preferred versions contained herein.

What is claimed is:

1. A method for the decontamination and disposal of a porous material containing body-fluids comprising:
   a) supplying a bag having enclosed therein a disinfecting agent, the bag being sealed to prevent the activity of the disinfecting agent from being significantly diminished by evaporation or reaction with ambient air, b) opening the bag at the time of use, c) placing at least a portion of a porous material containing body-fluids in contact with the disinfecting agent to form a combination, the combination being positioned in the opened bag, d) sealing the bag to prevent its contents from exiting the bag or ambient air from entering the bag, e) causing the disinfecting agent to penetrate the porous material and contact the body-fluids, and f) disposing of the sealed bag and its contents.

2. A method of decontaminating the disposing of an absorbent pad containing menstrual blood comprising:

a) supplying a non-porous bag having a first outer wall and a second outer wall spaced from the first wall, the bag containing an object located between the first outer wall and the second outer wall, the object comprising an disinfecting material, the first outer wall of the bag having a openable portion capable of being opened no greater than a preset length to allow the object located between the first and second outer walls to be removed through the opening thus formed, the bag further having a flap attached thereto, the flap having an inner surface positioned to cover the openable portion after opening, the flap carrying an adhesive strip on the inner surface, the adhesive strip being larger than the largest preset length of the opening, the adhesive being covered by a removable protective film, b) creating an opening in the openable portion of the first wall of the bag, c) removing the disinfecting material from the bag and bringing the disinfecting material into contact with a pad containing menstrual blood to define a combination, d) placing the pad and the disinfecting material combination back through the opening int eh bag wall so that the pad and disinfecting material combination is fully contained in the bag, e) removing the protective film to expose the adhesive on the flap, f) placing the adhesive strip on the flap over the opening in the first wall of the bag so that the adhesive strip completely surrounds the opening, and g) disposing of the bag and its contents in a suitable waste receptacle.

3. The method of claim 2 wherein the disinfecting material is chosen from the group consisting of chlorine-releasing materials, peroxide-releasing materials, iodine-releasing materials and a combination of two or more of the chlorine-peroxide- and iodine-releasing materials.

4. The method of claim 2 wherein the disinfecting material is made available in a form chosen from the group consisting of a liquid carried by a porous substrate, a dry form which can be activated by contacting the disinfecting material with moist blood on the pad, and a dry or liquid disinfecting material enclosed in a frangible container.

5. A combination of a container having, a disinfecting agent and a carrier for the disinfecting agent enclosed within the container comprising:

a bag with means capable of being opened and resealed a single time, the means comprising an openable portion in a first wall thereof and means for sealing the openable portion after opening, the sealing thereof not being reversible without destroying the sealing means, the bag being non-pervious to its contents prior to the openable opening portion in the wall, the opening formed being suitable for removal from and reinsertion of the carrier and the disinfecting agent into the bag and being non-pervious to its contents after the opening in the wall is resealed.

6. The container of claim 5 wherein the bag is rectangular in shape, a flap of a fixed width is attached to and extends along a first end of the bag, the width of the flap being the distance from the first end of the bag to an edge of the flap parallel to the first end of the bag, and the bag has a slit of a fixed length in the first wall of the bag, the slit being parallel to the first end of the bag and spaced from the first end of the bag a distance less than the width of the flap, the flap having an adhesive strip applied to a first surface of the flap parallel to the bag first end and being longer in length than the length of the slit, the adhesive located so that the flap can be folded at the juncture of the bag and flap, and, after folding, the adhesive on the flap adheres to the first wall of the bag and completely covers and surrounds the slit.

7. A system for receiving, decontaminating and disposing of a blood-containing menstrual pad comprising:

a non-porous bag containing structure for opening and resealing the bag a single time, and a disinfecting agent for microorganisms in blood contained in the bag, the structure for opening and resealing the bag being an openable portion in a first wall thereof and means for sealing the openable portion after opening, the sealing thereof not being reversible without destroying the sealing means, the bag being non-pervious to its contents prior to opening of the openable portion in the wall, the openings formed being suitable for placing a blood containing menstrual pad into contact with the disinfecting agent in the bag and being non-pervious to its contents after the opening in the wall is resealed, wherein the disinfecting agent is chosen from the group consisting of chlorine-releasing materials, peroxide-releasing materials, iodine-releasing materials and a combination of two or more of the chlorine-peroxide-, and iodine-releasing materials, and the disinfecting agent is made available in a form chosen from the group consisting of a liquid carried by a porous substrate, a dry form which can be activated by contacting the disinfecting agent with moist blood on the pad, and a dry or liquid disinfectant material enclosed in a frangible container.

8. A process to destroy microorganisms in menstrual blood comprising:

bringing a pad containing menstrual blood into contact with a disinfecting agent, placing the pad along with the disinfecting agent into a bag, and sealing the bag so its contents can not be removed without destructively opening the bag, the disinfecting agent being initially enclosed in the bag, the bag being openable once to gain access to the disinfecting agent.

* * * * *